United States Patent [19]

Chen et al.

[11] Patent Number: 5,275,809
[45] Date of Patent: Jan. 4, 1994

[54] AMPHOLYTE TERPOLYMERS PROVIDING SUPERIOR CONDITIONING PROPERTIES IN SHAMPOOS AND OTHER HAIR CARE PRODUCTS

[75] Inventors: Shih-Ruey T. Chen, Pittsburgh; Craig W. Vaughan, Freedom, both of Pa.

[73] Assignee: Calgon Corporation, Pittsburgh, Pa.

[21] Appl. No.: 948,339

[22] Filed: Sep. 21, 1992

Related U.S. Application Data

[63] Continuation-in-part of Ser. No. 722,638, Jun. 28, 1991, abandoned.

[51] Int. Cl.$^5$ .................. A61K 7/075; A61K 7/09
[52] U.S. Cl. .......................... 424/70; 424/71; 424/DIG. 2; 424/78.08; 252/DIG. 13
[58] Field of Search ............. 424/70, 71, 78.1, 78.12, 424/78.08, DIG. 2

[56] References Cited

U.S. PATENT DOCUMENTS

| | | | |
|---|---|---|---|
| 3,986,825 | 12/1976 | Sokol | 424/70 |
| 4,128,631 | 12/1978 | Lundmark et al. | 424/70 |
| 4,131,576 | 12/1978 | Iovine et al. | 260/17.4 |
| 4,175,572 | 11/1979 | Hsiung et al. | 424/70 |
| 4,455,240 | 6/1984 | Costello | 424/70 |
| 4,460,477 | 7/1984 | Costello et al. | 252/8 |
| 4,484,631 | 11/1984 | Sherwood et al. | 166/274 |
| 4,533,708 | 8/1985 | Costello | 526/295 |
| 4,578,267 | 3/1986 | Salamone | 424/70 |
| 4,590,249 | 5/1986 | Cabestant et al. | 526/287 |
| 4,710,374 | 12/1987 | Grollier et al. | 424/71 |
| 4,719,099 | 1/1988 | Grollier | 424/47 |
| 4,803,071 | 2/1989 | Iovine et al. | 424/70 |
| 4,806,345 | 2/1989 | Bhattacharyya | 424/70 |
| 4,842,849 | 6/1989 | Grollier et al. | 424/70 |
| 4,859,458 | 8/1989 | Salamone et al. | 424/70 |
| 4,963,348 | 10/1990 | Bolich | 424/70 |
| 4,996,059 | 2/1991 | Grollier | 424/70 |

FOREIGN PATENT DOCUMENTS

| | | |
|---|---|---|
| 0217274 | 9/1985 | European Pat. Off. |
| 308189 | 9/1988 | European Pat. Off. |
| 308190 | 9/1988 | European Pat. Off. |
| 353987 | 8/1989 | European Pat. Off. |
| 2113245 | 1/1983 | United Kingdom |

*Primary Examiner*—Thurman K. Page
*Assistant Examiner*—Raj Bawa
*Attorney, Agent, or Firm*—William C. Mitchell

[57] ABSTRACT

Ampholyte terpolymer conditioning additives for hair care products are disclosed which improve wet and dry hair combability, especially detangling and reduced static flyaway, sheen, and fixative properties, especially curl retention. The ampholyte terpolymers may have a weight average molecular weight of from about 10 thousand to 10 million, and comprise (a) from at least 1 to as much as 95 weight percent of the nonionic monomer acrylamide (AM), (b) from at least 5 to as much as 80 weight percent of the cationic monomer dimethyldiallylammonium chloride (DMDAAC), and (c) from at least 1 to as much as 75 weight percent of the anionic monomer 2-acrylamido-2-methylpropane sulfonic acid (AMPSA), with optionally up to 50% of said anionic monomer AMPSA being replaced with the anionic monomer acrylic acid (AA). The ampholyte terpolymers are added to hair care product formulations in amounts ranging from 0.1–10% by weight. They are particularly compatible with anionic surfactant shampoos, providing clear formulations without the loss of conditioning properties described above.

15 Claims, No Drawings

AMPHOLYTE TERPOLYMERS PROVIDING SUPERIOR CONDITIONING PROPERTIES IN SHAMPOOS AND OTHER HAIR CARE PRODUCTS

This is a continuation-in-part of application Ser. No. 07/722,638 filed Jun. 28, 1991 now abandoned.

BACKGROUND OF THE INVENTION

1. Field of the Invention

The present invention relates to compositions and methods for treating hair in which a cosmetically acceptable medium is used which contains from 0.1–10% by weight of an ampholyte terpolymer. In particular, the cosmetically acceptable medium is an anionic surfactant-containing shampoo, and the ampholyte terpolymer exhibits good compatibility therewith in that the final solution is clear.

The surface properties of human hair are, of course, of basic interest in cosmetic science, and there has thus been a long-standing desire to discover ingredients which will beneficially affect the topical and bulk condition of this keratinous substrate. Such ingredients must have adequate adherent properties, so that they are not only adsorbed initially, but are also retained on exposure to water. This property is referred to as "substantivity", i.e., the ability of a material to be adsorbed onto the keratin of the hair and to resist removal by water rinse-off.

As indicated, human hair is composed of keratin, a sulfur-containing fibrous protein. The isoelectric point of keratin, and thus of the hair of which it is composed, is in the pH range of 3.2–4. Thus, at the pH of typical shampoo conditions, hair carries a net negative charge. Consequently, cationic polymers have long been used as conditioners in shampoo formulations, or as a separate treatment, in order to improve the wet and dry combability of the hair. The substantivity of the cationic polymers for negatively charged hair leads to film formation that facilitates detangling in wet hair combing and a reduction in static flyaway in dry hair combing. The cationic polymers also impart softness and suppleness to the hair.

When cationic polymers are added to shampoos containing anionic surfactants, formation of highly surface active association complexes takes place which imparts improved foam stability to the shampoo. Maximum surface activity and foam stability, or lather, are achieved at near stoichimetric ratios of anionic sufactant:cationic polymer, where the complex is least water soluble. All cationic conditioners exhibit some incompatibility at some of these ratios. Compatibility gives a commerically more desirable clear formulation, while incompatibility leads to a haze or precipitation, which is aesthetically less desirable.

Hair fixative properties such as curl retention, are directly related to the film forming properties of the cationic monomers, as well as to molecular weight, with performance increasing with increasing molecular weight. However, the fixative properties conferred by the cationic monomers tend to have a reciprocal relationship to the other conditioning properties, i.e., good curl retention means that wet combability, for example, will suffer, and vice versa.

Surprisingly, it has been found that it is possible, by adjusting the weight proportions of the components of the ampholyte terpolymers of the present invention, to retain a desired balance of the beneficial conditioning properties conferred by each of those components. Thus, it is possible to keep the desired properties of substantivity, combability and feel, while at the same time improving anionic surfactant compatibility, curl retention, sheen, and static reduction properties. It is also possible to selectively optimize one or a subset of these conditioning properties, by proper proportioning of the components and their molecular weights. This may be a desired course of action responsive to an expression of consumer group preference for one or another of these various conditioning properties, depending on the makeup of that consumer group.

As already indicated, it is a preferred embodiment of the present invention to add the ampholyte terpolymers directly to an anionic surfactant-containing shampoo. Other embodiments are contemplated, however. Thus, excellent results have been achieved with treatments usually followed by rinsing, such as shampooing, but have also been achieved with treatments with lotions or creams followed by rinsing, which are used to obtain hair-conditioning effects and are applied before or after coloring, bleaching, shampooing, perming or straightening.

Thus, the compositions according to the present invention can also be used in the form of coloring products, setting lotions, blow-drying lotions, restructuring lotions or bleaching, perming or straightening products.

2. Brief Description of the Prior Art

Heretofore, hair conditioning additives have been largely of three different types: cationic polymers, proteins or protein derivatives, and fatty quaternary ammonium compounds. Commonly used cationic polymers include: quaternary nitrogen-containing hydroxyethyl cellulose compounds, copolymers of vinylpyrrolidone and dimethylaminoethylmethacrylate, and amino functional polydimethylsiloxane. Hydrolyzed animal protein has been frequently used as a hair conditioner. Also used are natural products such as collagen and casein. Suitable quaternary ammonium compounds include such products as stearyl dimethyl ammonium chloride.

Conditioning additives comprising copolymers of dimethyldiallylammonium chloride and other monomers are well known; see, e.g., EP 308189 (with acrylamide); EP 0 308 190 and U.S. Pat. No. 4,803,071 (with hydroxyethyl cellulose). The use of such polymers in cosmetics is also described in Sykes et al., *Drug Cosmet. Ind.*, 126(2), 62, 64, 66, 68, 136 (1980). Amphoteric betaines have also been employed in cosmetic compositions; see GB 2,113,245 which discloses use of betainized dialkylaminoalkyl(meth)acrylate together with a cationic polymer.

The use of polymers of dimethyldiallylammonium chloride alone in hair treatment compositions is also known. See, e.g., U.S. Pat. Nos. 4,175,572 and 3,986,825.

While the use of various combinations of cationic, anionic and/or nonionic polymers as additives for hair conditioning compositions has been suggested heretofore, there has been no appreciation that a significant improvement in all of the desired hair conditioning properties could be obtained by employing an ampholyte terpolymer of the type used in the compositions and methods of the present invention.

For example, U.S. Pat. Nos. 4,578,267 and 4,859,458 disclose hair conditioning polymers containing alkoxylated nitrogen salts of sulfonic acid which may also include additional monomers that may be neutral, anionic and/or cationic. While these inlcude acrylamide, acrylic acid and dimethyldiallylammonium chloride, there is no suggestion of the ampholyte terpolymers of the present invention.

EP 0 353 987 discloses polymers for water-rinsable personal care products including conditioning shampoos, comprising a cationic monomer including dimethyldiallylammonium chloride, a monomer that carries a pendant group $A_nR$ where n is 0 or a positive integer, A is ethyleneoxy and R is a hydrocarbyl group of 8 to 30 carbon atoms, and optionally a nonionic and/or an anionic monomer. However, there is no suggestion of the ampholyte terpolymers of the present invention.

U.S. Pat. No. 4,710,374 discloses compositions suitable for treating the hair comprising a cationic polymer including poly(dimethyldiallylammonium chloride), and an anionic latex, but there is no suggestion of the ampholyte terpolymers of the present invention.

U.S. Pat. No. 4,842,849 discloses compositions suitable for treating the hair comprising at least one cationic polymer including poly(dimethyldiallylammonium chloride), and at least one anionic polymer containing vinylsulfonic groups, optionally copolymerized with acrylamide. The cationic polymer may be an amphoteric polymer as defined, but none of these combinations suggest the ampholyte terpolymers of the present invention.

EP 0 080 976 discloses aqueous hair-cosmetic compositions containing a surface active polymeric acrylic-based quaternary ammonium salt, a monomeric or oligomeric ammonium salt, and a surface active nonionic, anionic or zwitterionic component. The ampholyte terpolymers of the present invention are not suggested.

U.S. Pat. No. 4,128,631 discloses a method of imparting lubricity to keratinous substrates such as skin or hair by contacting said substrates with a salt of 2-acrylamido-2-methylpropane sulfonic acid (AMPSA) having a molecular weight of from 1-5 million. The ampholyte terpolymers of the present invention and their unexpected advantageous properties are not suggested.

The ampholyte terpolymers of the present invention are regarded as novel compositions of matter because of their unique properties, and their use as hair conditioning additives has not heretofore been suggested.

Terpolymers of acrylamide/dimethyldiallylammonium chloride/acrylic acid are disclosed in U.S. Pat. Nos. 4,455,240; 4,460,477; 4,484,631; and 4,533,708; however, nowhere is there a suggestion that those terpolymers might be used as conditioning additives for hair products.

A graft copolymer of acrylamide/acrylic acid/amylopectin/dimethyldiallylammonium chloride is disclosed in U.S. Pat. No. 4,131,576, but is only suggested for use as a pigment retention agent in papermaking.

The ampholyte terpolymers of the present invention represent a significant advance in the state of the hair conditioning art and afford properties which are a surprising improvement over those possessed by the hair conditioning additives in the prior art described above. In contrast to such additives, the ampholyte terpolymers of the present invention provide either an optimized combination of all hair conditioning properties, or else an optimized subset of such properties, which include: detangling, wet combability, wet feel, dry combability, dry feel, sheen, static flyaway control, and curl retention. A detailed demonstration of the dramatic improvement in these properties is set out further below.

SUMMARY OF THE INVENTION

The present invention relates to a composition for treating hair in which a cosmetically acceptable medium is used which contains from 0.1-10% by weight of a water soluble ampholyte terpolymer having a weight average molecular weight of from about 10 thousand to 10 million, comprising (a) from at least 1 to as much as 95 weight percent of the nonionic monomer acrylamide (AM), (b) from at least 5 to as much as 80 weight percent of the cationic monomer dimethyldiallylammonium chloride (DMDAAC), and (c) from at least 1 to as much as 75 weight percent of the anionic monomer 2-acrylamido-2-methylpropane sulfonic acid (AMPSA), with optionally up to 50% of said anionic monomer AMPSA being replaced with the anionic monomer acrylic acid (AA).

In particular, the cosmetically acceptable medium is an anionic surfactant-containing shampoo, and the ampholyte terpolymer exhibits good compatibility therewith in that the final solution is clear.

The present invention also relates to a method of treating hair which comprises applying to hair a cosmetically acceptable medium containing from 0.1-10% by weight of a water soluble ampholyte terpolymer having a weight average molecular weight of from about 10 thousand to 10 million, comprising (a) from at least 1 to as much as 95 weight percent of the nonionic monomer acrylamide (AM), (b) from at least 5 to as much as 80 weight percent of the cationic monomer dimethyldiallylammonium chloride (DMDAAC), and (c) from at least 1 to as much as 75 weight percent of the anionic monomer 2-acrylamido-2-methylpropane sulfonic acid (AMPSA), with optionally up to 50% of said anionic monomer AMPSA being replaced with the anionic monomer acrylic acid (AA).

In particular, the cosmetically acceptable medium is an anionic surfactant-containing shampoo, and the ampholyte terpolymer exhibits good compatibility therewith in that the final solution is clear.

The present invention further relates to a method of treating hair in conjunction with the shampooing thereof with an anionic sufactant-containing shampoo, so as to improve the conditioning thereof with respect to the properties of detangling, wet combability, wet feel, dry combability, dry feel, sheen, static flyaway control, and curl retention comprising applying to said hair a composition compatible with said anionic surfactant-containing shampoo such that a clear formulation thereof is provided without the loss of said conditioning properties, wherein said composition comprises a cosmetically acceptable medium containing from 0.1-10% by weight of a water soluble ampholyte terpolymer having a weight average molecular weight of from about 10 thousand to 10 million, comprising (a) from at least 1 to as much as 95 weight percent of the nonionic monomer acrylamide (AM), (b) from at least 5 to as much as 80 weight percent of the cationic monomer dimethyldiallylammonium chloride (DMDAAC), and (c) from at least 1 to as much as 75 weight percent of the anionic monomer 2-acrylamido-2-methylpropane sulfonic acid (AMPSA), with optionally up to 50% of said anionic monomer AMPSA being replaced with the anionic monomer acrylic acid (AA).

DETAILED DESCRIPTION OF THE INVENTION

As already indicated, the present invention relates to a composition for treating hair in which a cosmetically acceptable medium is used which contains from 0.1–10% by weight of a water soluble ampholyte terpolymer having a weight average molecular weight of from about 10 thousand to 10 million, comprising (a) from at least 1 to as much as 95 weight percent of the nonionic monomer acrylamide (AM), (b) from at least 5 to as much as 80 weight percent of the cationic monomer dimethyldiallylammonium chloride (DMDAAC), and (c) from at least 1 to as much as 75 weight percent of the anionic monomer 2-acrylamido-2-methylpropane sulfonic acid (AMPSA), with optionally up to 50% of said anionic monomer AMPSA being replaced with the anionic monomer acrylic acid (AA).

COMPONENTS OF THE AMPHOLYTE TERPOLYMERS

Turning to each of the components of the ampholyte terpolymer in turn, the nonionic monomer acrylamide may be represented by the following formula:

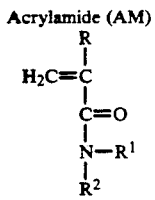

Acrylamide (AM)

where R is H or $CH_3$; and $R^1$ and $R^2$ are independently H, $C_{1-4}$alkyl, $CH_2OCH_3$, $CH_2OCH_2CH(CH_3)_2$, $(CH_2CH_2O—)_x—H$, where $x=1–50$, or phenyl, or together are $C_{3-6}$cycloalkyl.

The preferred acrylamide monomer is the simplest, i.e., that where R, $R_1$, and $R_2$ are all H. However, the other acrylamide derivatives within the scope of the formula set out above are also contemplated to be a part of the present invention, since they are well known in the art of hair conditioning, where polyacrylamide and copolymers using acrylamide monomer are well known.

The nonionic acrylamide monomer portion of the ampholyte terpolymers of the present invention is present in an amount of from 1 to 95 weight percent of the total terpolymer. Preferably, this amount is from 5 to 80 weight percent, and most preferably, this amount is from 10 to 50 weight percent. The acrylamide contributes to the film forming capacity of the total terpolymer and thus improves curl retention. It also improves the static flyaway control of the overall terpolymer.

Since, in a preferred embodiment of the present invention the amounts of cationic and anionic components are such that the net charge of the overall terpolymer is near zero, there is a tendency in such preferred terpolymers to form water insoluble polysalt complexes. The presence of acrylamide serves to enhance the water solubility of the terpolymers in those situations.

The next component of the ampholyte terpolymers of the present invention is the cationic monomer, i.e., derivatives of diallylamine, especially dimethyldiallylammonium chloride (DMDAAC), which may be represented by the following formula:

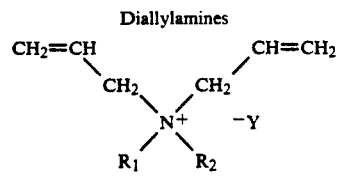

Diallylamines where $R_1$ and $R_2$ are independently H or $C_{1-12}$alkyl. The moiety $^-Y$ is a suitable anion, such as halide, preferably $^-Cl$, but also including sulfate, and so forth. It is within the skill of the artisan to choose such an anion. The preferred cationic monomer of the present invention is dimethyldiallylammonium chloride (DMDAAC), i.e., where $R_1$ and $R_2$ are $CH_3$.

The cationic dimethyldiallylammonium chloride monomer portion of the ampholyte terpolymers of the present invention is present in an amount of from 5 to 80 weight percent of the total terpolymer. Preferably, this amount is from 15 to 60 weight percent. The dimethyldiallylammonium chloride contributes to all of the hair conditioning properties except for curl retention. As a cationic monomer it possesses the inherent substantivity necessary for the overall terpolymer to function. It also provides the basic improvement in detangling, wet and dry hair combability, sheen and feel, and control of static flyaway. However the dimethyldiallylammonium chloride does not possess good film forming properties, and thus does not play any substantial role in improving curl retention.

The final component of the ampholyte terpolymers of the present invention is the anionic monomer 2-acrylamido-2-methylpropane sulfonic acid (AMPSA), with optionally up to 50% of said anionic monomer AMPSA being replaced with the anionic monomer acrylic acid (AA), both of which may be represented by the following formulas:

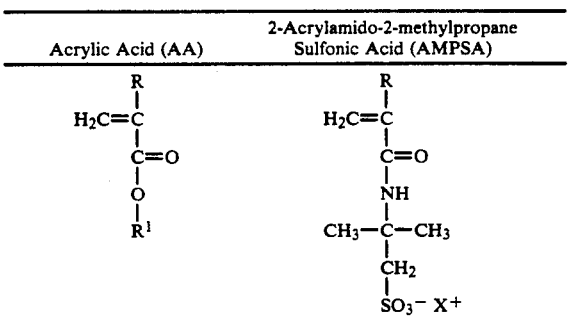

| Acrylic Acid (AA) | 2-Acrylamido-2-methylpropane Sulfonic Acid (AMPSA) |
|---|---| where R is H or $CH_3$; $R^1$ is $X^+$, H, $C_{1-4}$alkyl, $CH_2CH_2OH$, $(CH_2CH_2O—)_x—H$, where $x=1–50$, or phenyl, and $X^+$ is a suitable cation forming a salt of the carboxylic or sulfonic acid, such as sodium, potassium, ammonium, monoethanolamine, etc., all of which are well known and within the ordinary skill of the artisan to choose. Preferred anionic monomers of this type are acrylic acid and 2-acrylamido-2-methylpropane sulfonic acid, respectively.

The anionic 2-acrylamido-2-methylpropane sulfonic acid (AMPSA) monomer portion of the ampholyte terpolymers of the present invention is present in an amount of from 1 to 75 weight percent of the total terpolymer. Preferably, this amount is from 5 to 40 weight percent. Optionally, up to 50% of this amount may be replaced by acrylic acid monomer, as defined above, although this is not preferred. For example, an ampholyte terpolymer of the present invention may contain 20% by weight of anionic monomer, 10% of which is AMPSA and 10% of which is AA. The anionic 2-acrylamido-2-methylpropane sulfonic acid (AMPSA), along with the acrylamide, contributes to the film forming capacity of the total terpolymer and thus improves curl retention. In amounts as little as 1-2 weight percent, the 2-acrylamido-2-methylpropane sulfonic acid, with optionally up to 50% of acrylic acid, measurably improves the compatibility of the overall terpolymer with the anionic surfactant of which a typical shampoo is made. It has also been found that the 2-acrylamido-2-methylpropane sulfonic acid, with optionally up to 50% of acrylic acid adds to the improvement of all of the hair conditioning properties already provided by the cationic component as discussed above. This result was unexpected, and is another indication of the unexpected properties of the ampholyte terpolymers of the present invention.

It is also possible to selectively optimize one or a subset of the desired conditioning properties described above, by proper proportioning of the components and their molecular weights. This may be a desired course of action responsive to an expression of particular consumer group preference for one or another of these various conditioning properties, depending on the makeup of that particular consumer group.

SPECIFIC AMPHOLYTE TERPOLYMERS

Examples of specific ampholyte terpolymers within the scope of the present invention are set out in the following table:

| SAMPLE NO. | WT. % AM | POLYMER COMPOSITION | | REDUCED VISC. (dl/g) | % NET CHARGE |
|---|---|---|---|---|---|
| | | DMCAAC | AMPSA | | |
| 56 | 50 | 22 | 28 | 6.9 | +0.1 |
| 41 | 50 | 30 | 10 + 10 AA | 5.9 | −0.1 |
| 58 | 50 | 15 | 35 | 7.7 | −7.9 |
| 61 | 50 | 40 | 10 | 4.7 | +20.0 |
| 94 | 60 | 30 | 10 | — | +12.8 |
| 92 | 49 | 37 | 14 | — | +16.3 |
| 73 | 50 | 40 | 10 | 4.8 | +20.0 |
| 93 | 16 | 32 | 52 | 4.6 | −3.9 |

MOLECULAR WEIGHTS

The molecular weight of the ampholyte terpolymers of the present invention may be within the broad range of from about 10 thousand to about 10 million. The molecular weights of most of the specific terpolymers described herein are within the range of about 4 to 8 million. However, it is generally conceded that for polymers used in hair conditioning, molecular weights over about 1 million add little to the effectiveness of those polymers in terms of hair conditioning properties, with the possible exception of curl retention. At the other end of the scale, polymers with relatively low molecular weights may also be effective in providing hair conditioning properties. For example, a commercial hair conditioning polymer of the Polymer JR (Reg. TM) series, has a molecular weight of about 30 thousand. The ampholyte terpolymers of the present invention are also useful in weight average molecular weight ranges below 1 million, and even below 100 thousand, although generally the preferred molecular weight range will be from about 500 thousand to 5 million.

Reduced viscosity (dl/g) is used herein as an approximate measure of the weight average molecular weight of the ampholyte terpolymers of the present invention. The values used herein represent a capillary viscosity measured with a Ubbelohde Capillary Viscometer at 0.05% concentration of polymer in a 1M NaCl solution, pH 7, at 30° C. The resulting value is calculated in accordance with methods well known in the art.

PREPARATION (POLYMERIZATION)

The ampholyte terpolymers of the present invention may be prepared in a straightforward manner by using the process described immediately below.

For each terpolymer composition the appropriate weights of aqueous acrylamide and DMDAAC monomers are charged to a glass reactor equipped with stirring. The volume of 2-acrylamido-2-methylpropane sulfonic acid monomer, and optionally also of acrylic acid monomer where this is present, to be added is diluted first with deionized water and then added to the reactor with vigorous stirring to give a total monomer concentration of 14-20%. The monomer mixture is adjusted to pH 6.5 with dilute NaOH, heated to 55° C., and purged with nitrogen for at least thirty minutes. Polymerization is initiated by adding $5 \times 10^{-2}$ mole % of sodium persulfate and $2.4 \times 10^{-3}$ mole % of sodium bisulfite. After the peak exotherm is reached, additional dilution water and sodium bisulfite are added to scavenge any residual monomer and to dilute the final product to 4-8% polymer solids.

Further details of the method of preparation are set out in the description of specific embodiments further below.

COSMETICALLY ACCEPTABLE MEDIA

The ampholyte terpolymers of the present invention are used as compositions for treating hair by incorporating them in a cosmetically acceptable medium in amounts of from 0.1-10% by weight of said terpolymer, and preferably in an amount of from 0.5 to 5% by weight of said terpolymer.

These compositions can be presented in various forms, i.e., various cosmetically acceptable media, such as a liquid, cream, emulsion, gel, thickening lotion or powder; they can contain water and also any cosmetically acceptable solvent, in particular monoalcohols, such as alkanols having 1 to 8 carbon atoms, like ethanol, isopropanol, benzyl alcohol and phenylethyl alcohol, polyalcohols, such as alkylene glycols, like glycerine, ethylene glycol and propylene glycol, and glycol ethers, such as mono-, di- and tri-ethylene glycol mono-alkyl ethers, for example ethylene glycol monomethyl ether, ethylene glycol monomethyl ether and diethylene glycol monomethyl ether, used singly or in a mixture. These solvents can be present in proportions of up to as much as 70% by weight, relative to the weight of the total composition.

These compositions can also be packaged as an aerosol, in which case they can be applied either in the form of an aerosol spray or in the form of an aerosol foam.

As the propellant gas for these aerosols, it is possible to use, in particular, dimethyl ether, carbon dioxide, nitrogen, nitrous oxide and volatile hydrocarbons, such as butane, isobutane, propane and, possibly, chlorinated and fluorinated hydrocarbons, although the latter are falling into increasing environmental disfavor.

Preferred compositions can also contain electrolytes, such as aluminum chlorhydrate, alkali metal salts, e.g., sodium, potassium or lithium salts, these salts preferably being halides, such as the chloride or bromide, and the sulphate, or salts with organic acids, such as the acetates or lactates, and also alkaline earth metal salts, preferably the carbonates, silicates, nitrates, acetates, gluconates, pantothenates and lactates of calcium, magnesium and strontium.

These compositions can also be presented in the form of a powder or of lyophilisates to be diluted before use.

The compositions according to the present invention can contain any other ingredient normally used in cosmetics, such as perfumes, dyestuffs which can serve to color the composition itself or the fibres of the hair, preservatives, sequestering agents, thickeners, silicones, softeners, foam synergistic agents, foam stabilisers, sun filters, peptising agents and also anionic, non-ionic, cationic or amphoteric surface-active agents or mixtures thereof.

These compositions can be used, in particular, in the form of a shampoo, a rinsing lotion, a cream or a treatment product which can be applied before or after coloring or bleaching, before or after shampooing, before or after perming or before or after straightening, and can also adopt the form of a coloring product, a setting lotion, a brushing lotion, a bleaching product, a perming product or a straightening product.

A particularly preferred embodiment consists of use in the form of a shampoo for washing the hair.

In this case, these compositions contain anionic, cationic, nonionic or amphoteric surface-active agents typically in an amount from 3 to 50% by weight, preferably 3 to 20%, and their pH is 3 to 10.

A list of the surface-active agents which can be used according to the invention is given in U.S. Pat. No. 4,240,450; 4,445,521; and 4,719,099.

Another preferred embodiment consists of use in the form of a rinsing lotion to be applied mainly before or after shampooing. These lotions are typically aqueous or aqueous-alcoholic solutions, emulsions, thickened lotions or gels. If the compositions are presented in the form of an emulsion, they can be nonionic, anionic or cationic. The nonionic emulsions consist mainly of a mixture of an oil and/or a fatty alcohol with a polyoxyethyleneated alcohol, such as polyoxyethyleneated stearyl or cetyl/stearyl alcohol, and cationic surface-active agents can be added to these compositions. The anionic emulsions are formed essentially from soap.

If the compositions are presented in the form of a thickened lotion or a gel, they contain thickeners in the presence or absence of a solvent. The thickeners which can be used are especially carbopol, xanthan gums, sodium alginates, gum arabic and cellulose derivatives, and it is also possible to achieve thickening by means of a mixture of polyethylene glycol stearate or distearate or by means of a mixture of a phosphoric acid ester and an amide. The concentration of thickener is suitably 0.05 to 15% by weight. If the compositions are presented in the form of a styling lotion, shaping lotion or setting lotion, they generally comprise, in aqueous, alcoholic or aqueous-alcoholic solution, the ampholyte terpolymers defined above.

If the compositions of the invention are intended for use in the dyeing of keratin fibres, and in particular human hair, they contain at least one oxidation dyestuff precursor and/or one direct dyestuff, in addition to the ampholyte terpolymer. They can also contain any other adjuvant normally used in this type of composition.

The pH of the dyeing compositions is generally 7 to 11 and can be adjusted to the desired value by adding an alkalizing agent.

The composition according to the present invention can also be used for waving or straightening the hair. In this case, the composition contains, in addition to the ampholyte terpolymer, one or more reducing agents and, if appropriate, other adjuvants normally used in this type of composition; such compositions are intended for use conjointly with a neutralizing composition.

EXAMPLES OF PREFERRED EMBODIMENTS

The following examples demonstrate hair conditioning improvement results obtained with specific ampholyte terpolymers of the present invention, but are not intended to in any way limit the scope of the present invention. The results are compared to those obtained in the same tests (although not at the same time) with a commercial product, Gafquat 755N (Reg. TM), and deionized water (DI).

EXAMPLE 1

Wet Hair: Detangling, Combability and Feel

The following procedures were used to evaluate wet hair detangling, combability and feel:

1. Eighteen 2 grams tresses of bleached hair (supplied by Ruth L. Weintraub Co., Inc., 420 Madison Avenue, New York, NY 10017), 8 inches in length, were prepared for testing. The ends were trimmed to equal lengths (6 inches; length=L); and the root end of the hair was placed into a clamp.
2. All of the tresses were washed in clean denatured alcohol (100%), by dipping each tress in the denatured alcohol and swirling 3 times. The tresses were allowed to dry by hanging on a peg board, at room temperature for 1 hour.
3. Using 6 tresses per treatment, each tress was immersed in one of the following three test solutions (the pH of these solutions was adjusted to 6.0±0.1 with citric acid or NaOH):
   a) Terpolymer solution, 0.5% Solids
   b) Gafquat 755N (Reg. TM) solution, 0.5% Solids
   c) deionized (DI) water.
   Each tress was allowed to soak in the solution for 3 minutes and was then rinsed under running deionized water for 2 minutes.
4. After the 2 minute rinse, each trees was evaluated for detangling, wet hair comb and wet hair feel. The detangling was evaluated by holding the clamp of the tress in one hand and using the other hand to comb the tress twice with the coarse end of the comb. The tress was then combed 5 times to remove all the tangles and the tress was combed twice with the fine end of the comb to evaluate wet hair comb. The tresses were evaluated and rated for detangling and wet hair combability in accordance with the following scale:
   4=Excellent=No snags
   3=Very Good=Very few snags
   2=Good=Few snags
   1=Fair =Many snags
   0=Poor=Very many snags
   The wet hair feel was evaluated by the subjective feel to the fingers of each tress. The combs [Goody (Reg. TM), H. Goodman & Sons, Inc., NY 10001] used for these tests were 7¼"×1½". The teeth on the course end of the comb were spaced ⅛" apart and the teeth on the fine end of the comb were spaced 1/16" apart.

The average of the results obtained in these tests are illustrated in the following table of values, in which WH=Wet Hair, DT=Detangling, and COMB=Combability:

TABLE 1

| SAMPLE NO. | WT. % AM | POLYMER COMPOSITION DMDAAC | AA | AMPSA | WH DT | WH COMB | WH FEEL |
|---|---|---|---|---|---|---|---|
| 56 | 50 | 22 | 0 | 28 | 1 | 2 | 1 |
| 41 | 50 | 30 | 10 | 10 | 4 | 4 | 4 |
| 58 | 50 | 15 | 0 | 35 | 4 | 4 | 4 |
| 61 | 50 | 40 | 0 | 10 | 4 | 4 | 4 |
| 94 | 60 | 30 | 0 | 10 | 4 | 4 | 4 |
| 92 | 49 | 37 | 0 | 14 | 3 | 4 | 3 |
| 73 | 50 | 40 | 0 | 10 | 0 | 1 | 1 |
| GAFQUAT 755N (average) | | | | | 4 | 4 | 4 |
| DI WATER (average) | | | | | 0 | 0 | 0 |

EXAMPLE 2

Curl Retention

After the procedures were carried out as described in Example 1, the following procedures were used to evaluate curl retention:

5. A "curl paper" [Goody (Reg. TM), H. Goodman & Sons, Inc., N.Y. 10001] was folded around each hair tress, close to the clamp, and slid down the hair to cover all loose ends. The end of the hair tress was set on the left edge of the roller [medium snap-over roller 11/16" diameter, Sekine (Reg. TM) Corporation, New York, N.Y. 10003], and was wound three times around the roller so that it ended up on the right hand edge of the roller. When all of the tresses had been treated, the entire rack of tresses was placed in a 50% relative humidity room and allowed to set overnight (at least 12 hours).
6. After this 12 hour set period, a humidity chamber was placed in a 50% relative humidity room. The atmosphere in the humidity chamber was then raised to 70% relative humidity (approx. 30 minutes) by blowing air over a 20% (w/w) solution of aqueous ammonium chloride and into the humidity chamber.
7. The rollers were then removed from the tresses.
8. The initial lengths of all the tresses were recorded as the length from the clamp to the bottom of the curl (initial length=$L_o$).
9. The rack of curls was then placed in the humidity chamber at 70% relative humidity for 15 minutes.
10. The length ($L_t$) of each tress (from the clamp to the bottom of the curl) was then measured every 15 minutes for 2 hours.
11. The curl retention was calculated using the following formula:

$$\% \text{ Curl Retention} = \frac{L - L_t}{L - L_o} \times 100$$

The results obtained from these tests are illustrated in the following table of values:

TABLE 2

| SAMPLE NO. | WT. % AM | POLYMER COMPOSITION DMDAAC | AA | AMPSA | AVERAGE CURL RETENTION @ 60 (min) | 120 (min) |
|---|---|---|---|---|---|---|
| 56 | 50 | 22 | 0 | 28 | 54.1 | 44.4 |
| 41 | 50 | 30 | 10 | 10 | 60.1 | 50.2 |
| 58 | 50 | 15 | 0 | 35 | 53.2 | 45.0 |
| 61 | 50 | 40 | 0 | 10 | 70.9 | 59.2 |
| 94 | 60 | 30 | 0 | 10 | 42.2 | 34.9 |
| 92 | 49 | 37 | 0 | 14 | 43.9 | 38.3 |
| 73 | 50 | 40 | 0 | 10 | 51.9 | 45.9 |
| GAFQUAT 755N (average) | | | | | 64.4 | 53.9 |
| DI WATER (average) | | | | | 53.6 | 43.8 |

EXAMPLE 3

Dry Hair: Combability, Feel and Sheen

The following procedures, which followed those carried out as described above in Examples 1 and 2, were used to evaluate dry hair combability, feel and sheen:

12. The rack of tresses used for the curl retention evaluations described in the previous example was removed from the humidity chamber and placed on a lab bench. Then, 8 panelists evaluated the 3 sets of 6 tresses for "ease of dry combing," "feel of hair," and "sheen or luster." Each panelist rated each tress for the preceding categories according to the following rating scale:
Poor=0; Fair=1; Good=2; Very Good=3; Excellent=4.

The results obtained from these evaluations are illustrated in the following table of values, in which DH=Dry Hair and COMB=Combability:

TABLE 3

| SAMPLE NO. | WT. % AM | POLYMER COMPOSITION DMDAAC | AA | AMPSA | DH COMB | DH FEEL | SHEEN |
|---|---|---|---|---|---|---|---|
| 56 | 50 | 22 | 0 | 28 | 2.88 | 2.25 | 2.38 |
| 41 | 50 | 30 | 10 | 10 | 2.75 | 2.50 | 2.50 |
| 58 | 50 | 15 | 0 | 35 | 2.88 | 3.00 | 3.00 |
| 61 | 50 | 40 | 0 | 10 | 2.75 | 2.38 | 1.88 |
| 94 | 60 | 30 | 0 | 10 | 2.2 | 2.6 | 2.4 |
| 92 | 49 | 37 | 0 | 14 | 1.8 | 2.6 | 2.4 |
| 73 | 50 | 40 | 0 | 10 | 2.0 | 2.2 | 2.2 |
| GAFQUAT 755N (average) | | | | | 2.54 | 2.60 | 2.37 |
| DI WATER (average) | | | | | 2.64 | 2.69 | 2.76 |

EXAMPLE 4

Static Flyaway Control

The following procedures, which followed those carried out as described above in Examples 1, 2 and 3, were used to evaluate control of static flyaway:

13. When the preceding panelist evaluations were complete, one tress from each set (1-terpolymer, 1-Gafquat and 1-DI water) was wet under running DI water and combed until no tangles remained. These tresses were placed on a smaller peg board and put in the 50% relative humidity room overnight.
14. Each of the tresses was then placed on a peg board in front of a protractor. The tresses were combed 20 times, with the same stroke each time, and the angle of the hair was recorded. The static angle of the hair was determined by the hair strand which produced the largest angle for that tress.

The results obtained from this test are illustrated in the following table of values:

TABLE 4

| SAMPLE NO. | WT. % AM | POLYMER COMPOSITION | | | STATIC ANGLE (degrees) |
|---|---|---|---|---|---|
| | | DMDAAC | AA | AMPSA | |
| 56 | 50 | 22 | 0 | 28 | 70 |
| 41 | 50 | 30 | 10 | 10 | 40 |
| 58 | 50 | 15 | 0 | 35 | 30 |
| 61 | 50 | 40 | 0 | 10 | 45 |
| 94 | 60 | 30 | 0 | 10 | 20 |
| 92 | 49 | 37 | 0 | 14 | 70 |
| 73 | 50 | 40 | 0 | 10 | — |
| GAFQUAT 755N (average) | | | | | 55 |
| DI WATER (average) | | | | | 37 |

The following examples illustrate various cosmetically acceptable media for preparing hair care compositions using the ampholyte terpolymers of the present invention. In those Examples, the following terpolymer abbreviations are used:

| | Polyampholyte A: | |
|---|---|---|
| By weight: | 50% Acrylamide | = Sample No. 41 |
| | 30% DMDAAC | |
| | 10% Acrylic Acid | |
| | 10% AMPSA | |
| | Polyampholyte B: | |
| By weight: | 50% Acrylamide | = Sample No. 58 |
| | 15% DMDAAC | |
| | 35% AMPSA | |
| | Polyampholyte C: | |
| By weight: | 50% Acrylamide | = Sample No. 61 |
| | 40% DMDAAC | |
| | 10% AMPSA | |

EXAMPLE 5

Creme Rinse

| WT. % | INGREDIENT |
|---|---|
| 93.1 | H$_2$O |
| 1.2 | Cetyl Alcohol |
| 0.8 | Stearyl Alcohol |
| 1.0 | Sorbitan Oleate |
| 0.4 | Polysorbate-85 |
| 1.0 | Distearyldiammonium Chloride |
| 2.5 | Polyampholyte B |

In this formulation, the ampholyte terpolymer stabilized an otherwise unstable composition. The ampholyte terpolymer also improved combability, hair feel, and provided a feeling of increased hair body. Similar results would be expected at ampholyte terpolymer concentrations of 0.1 to 10.0% by weight.

EXAMPLE 6

Shampoo

| WT. % | INGREDIENT |
|---|---|
| 28.50 | Water |
| 32.30 | Ammonium Lauryl Sulfate |
| 31.40 | Ammonium Laureth Sulfate |
| 4.25 | Ammonium Dodecylbenzene Sulfonate |
| 3.40 | Lauramide DEA |
| 0.15 | Disodium EDTA |
| 3.0 | Polyampholyte A |

The ampholyte terpolymer in this product formulation was responsible for a better feeling shampoo with thicker feeling lather. The hair was easier to comb and had a feeling of greater body. Similar results would be expected at ampholyte terpolymer concentrations of 0.1 to 10.0% by weight.

EXAMPLE 7

Creme Type Rearranger

| WT. % | INGREDIENT |
|---|---|
| 68.95 | H$_2$O |
| 6.00 | Sodium Lauryl Sulfate |
| 7.90 | Cetearyl Alcohol and Ceteareth-20 |
| 6.00 | Cetyl Alcohol and Ceteareth-30 |
| 1.50 | Ethylene Glycol Monostearate |
| 0.15 | Sodium Dihydroxyethylglycinate |
| 7.50 | Ammonium Thioglycolate (60%) |
| 2.00 | Aqua Ammonia |
| 4.00 | Polyampholyte C |

This type of product formulation is applied to extremely curly hair and is combed into the hair. Hair treated in this way will be straightened. The presence the ampholyte terpolymer makes the hair noticeably easier to comb. Effective amounts of ampholyte terpolymer in this type of product will be from 0.20% to 15.00% by weight.

EXAMPLE 8

Hair Styling Glaze

| WT. % | INGREDIENT |
|---|---|
| 88.4% | Water |
| 1.10 | Hydroxypropyl Methylcellulose |
| 0.50 | Quaternium-80 |
| 10.00 | Polyampholyte B |

The ampholyte terpolymer in this formulation provides curl and style retention, and the ampholyte terpolymer should be effective for this purpose at concentrations of 0.5% to 20.0% by weight.

EXAMPLE 9

Permanent Wave Neutralizer

| WT. % | INGREDIENT |
|---|---|
| 91.92 | H$_2$O |
| 0.20 | Pentasodium Pentatate |
| 0.180 | Citric Acid |

| WT. % | INGREDIENT |
|---|---|
| 5.70 | Hydrogen Peroxide (35%) |
| 2.0 | Polyampholyte C |

The ampholyte terpolymer in this product formulation imparts conditioning to and improves combability of hair. The ampholyte terpolymer should be effective at concentrations of 0.1% to 10% by weight or more.

EXAMPLE 10

Hair Spray

| WT. % | INGREDIENT |
|---|---|
| 92.00 | Water |
| 1.00 | Acetamide MEA |
| 1.00 | Glycerin |
| 3.00 | Vinylcaprolactam/PVP/Dimethylaminoethylmethacrylate copolymer |
| 3.00 | Polyampholyte A |

The ampholyte terpolymer in this formulation increases the style holding properties while improving the flexibility of the second polymer. Similar results are obtained at ampholyte terpolymer concentrations of 0.3% to 10.0% by weight.

EXAMPLE 11

Hair Styling Gel

| WT. % | INGREDIENT |
|---|---|
| 91.75 | H$_2$O |
| 0.375 | Carbomer - 940 |
| 0.625 | Triethanolamine |
| 0.10 | Trisodium EDTA |
| 5.0 | PVP |
| 0.2 | Laureth-23 |
| 0.2 | Oleth-20 |
| 0.25 | Hexylene Glycol |
| 1.50 | Polyampholyte A |

The ampholyte terpolymer in this product formulation provides increased curl and style retention along with increased flexibility of the hair fixative film.

EXAMPLE 12

Procedure for Preparing Ampholyte Terpolymer 16/32/52 AM/DMDAAC/AMPSA

Equipment:

| Polymerization | Dilution |
|---|---|
| 2-1 Dewar Flask | 2-1 Resin Kettle |
| Condenser | Condenser |
| Nitrogen with flowmeter | Nitrogen with flowmeter |
| Two-turbine mixer | Three turbine mixer |
| Thermometer | Thermometer |
| | Constant Temperature variac |

Materials:

| | Polymerization | | Dilution |
|---|---|---|---|
| 151.9 | 48.97 Acrylamide | 600 g | 20% polymer gel |
| 226.7 g | 65.60 DMDAAC | 890 g | DI Water |
| 468.0 g | 50.5% Na AMPSA Sol. | 7.5 g | SMBS AA-23 |
| 950.6 g | DI Water | 1.5 g | Methyl Paraben |
| 0.15 g | Sodium EDTA | 0.3 g | Propyl Paraben |
| 1.5 g | Salicylic Acid | | |
| 75.8 g | 50% Sodium Hydroxide (to pH = 6.5) | | |
| 0.4 g | Sodium Persulfate | | |
| 0.0076 g | SMBS | | |
| 0.00076 g | CuSO4 | | |
| 0.76 g | Versenex 80 (pH = 6.5) | | |

Procedures:

In a 2,000 mL beaker are mixed acrylamide solution, DMDAAC solution, glacial acrylic acid, EDTA, salicylic acid and DI water. To the reaction mixture a 50% sodium hydroxide is added at ambient temperature until pH of 6.5 is reached. The solution is then heated to 60° C. and poured into the 2-1 Dewar flask; then a 1.0 SCFM nitrogen purge is begun. After the solution cools to 55° C. (about 30 minutes) the Versenex 80, followed by SMBS/CuSO$_4$ solution and sodium persulfate solution are added. After the solution exotherms to 57° C. (about 20 minutes), the agitation is stopped and the nitrogen line lifted to blanket and reduced to 0.1 SCFM. The reaction exotherms at about 92° C. after about 100 minutes. The resulting gel is allowed to set overnight. Then, 600 g of the 20% polymer gel is removed for dilution and charged to a 2-1 resin kettle to which DI water is added, mixed and heated to 80° C.

Nitrogen is blanketed at 0.1 SCFM, and then SMBS is added as a 10% solution and mixed into the diluted gel. Methyl and propyl paraben are dissolved in 200 g of DI water, dissolved and heated to 80° C. This solution is then added to the diluted polymer gel. This final solution is stirred overnight at 70° C. and decanted to give the terpolymer final product.

What is claimed is:

1. A composition for treating hair in which a cosmetically acceptable medium is used which contains from 0.1–10% by weight of a water-soluble ampholyte terpolymer having a weight average molecular weight of from about 10 thousand to 10 million, comprising:

(a) from at least 1 to as much as 95 weight percent of the nonionic monomer acrylamide (AM) of the following formula:

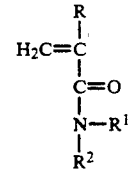

where R is H or CH$_3$; and R$^1$ and R$^2$ are independently H, C$_{1-4}$alkyl, CH$_2$OCH$_3$, CH$_2$OCH$_2$CH(CH$_3$)$_2$, (CH$_2$CH$_2$O—)$_x$—H, where x = 1–50, or phenyl, or together are C$_{3-6}$cycloalkyl;

(b) from at least 5 to as much as 80 weight percent of the cationic monomer dimethyldiallylammonium chloride (DMDAAC) of the following formula:

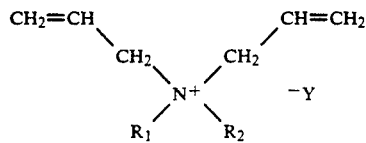

where $R_1$ and $R_2$ are independently H or $C_{1-12}$alkyl, and the moiety $^-Y$ is a suitable anion; and (c) from at least 1 to as much as 75 weight percent of the anionic monomer 2-acrylamido-2-methylpropane sulfonic acid (AMPSA), with optionally up to 50% of said anionic monomer AMPSA being replaced with the anionic monomer acrylic acid (AA), both of the following formulas:

| Acrylic Acid (AA) | 2-Acrylamido-2-methylpropane Sulfonic Acid (AMPSA) |
|---|---|
| $\begin{array}{c} R \\ \| \\ H_2C{=}C \\ \| \\ C{=}O \\ \| \\ O \\ \| \\ R^1 \end{array}$ | $\begin{array}{c} R \\ \| \\ H_2C{=}C \\ \| \\ C{=}O \\ \| \\ NH \\ \| \\ CH_3{-}C{-}CH_3 \\ \| \\ CH_2 \\ \| \\ SO_3^- \ X^+ \end{array}$ | where R is H or $CH_3$; $R^1$ is $X^+$, H, $C_{1-4}$alkyl, $CH_2CH_2OH$, $(CH_2CH_2O-)_x-H$, where x = 1-50, or phenyl, and $X^+$ is a suitable cation forming a salt of the carboxylic or sulfonic acid.

2. A composition according to claim 1 wherein the weight percent of AM is from 10 to 80, the weight percent of DMDAAC is from 15 to 60, and the weight percent of AMPSA is from 5 to 40.

3. A composition according to claim 1 wherein the ampholyte terpolymer is a member selected from the group consisting of:

| WT. % | POLYMER COMPOSITION | |
|---|---|---|
| AM | DMCAAC | AMPSA |
| 50 | 22 | 28 |
| 50 | 30 | 10 + 10 AA |
| 50 | 15 | 35 |
| 50 | 40 | 10 |
| 60 | 30 | 10 |
| 49 | 37 | 14 |
| 50 | 40 | 10 |
| 16 | 32 | 52 |

4. A composition according to claim 1 wherein the ampholyte terpolymer has a molecular weight of from about 500 thousand to about 5 million.

5. A composition according to claim 1 wherein the cosmetically acceptable medium is an anionic surfactant-containing shampoo.

6. A method of treating hair which comprises applying to hair a cosmetically acceptable medium containing from 0.1–10% by weight of a water-soluble ampholyte terpolymer having a weight average molecular weight of from about 10 thousand to 10 million, comprising:

(a) from at least 1 to as much as 95 weight percent of the nonionic monomer acrylamide (AM) of the following formula:

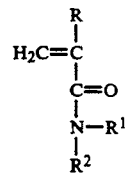

where R is H or $CH_3$; and $R^1$ and $R^2$ are independently H, $C_{1-4}$alkyl, $CH_2OCH_3$, $CH_2OCH_2CH(CH_3)_2$, $(CH_2CH_2O-)_x-H$, where x = 1-50, or phenyl, or together are $C_{3-6}$cycloalkyl;

(b) from at least 5 to as much as 80 weight percent of the cationic monomer dimethyldiallylammonium chloride (DMDAAC) of the following formula:

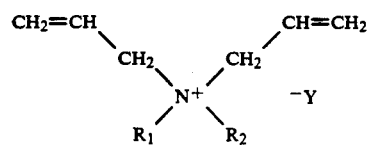

where $R_1$ and $R_2$ are independently H or $C_{1-2}$alkyl, and the moiety $^-Y$ is a suitable anion; and (c) from at least 1 to as much as 75 weight percent of the anionic monomer 2-acrylamido-2-methylpropane sulfonic acid (AMPSA), with optionally up to 50% of said anionic monomer AMPSA being replaced with the anionic monomer acrylic acid (AA), both of the following formulas:

| Acrylic Acid (AA) | 2-Acrylamido-2-methylpropane Sulfonic Acid (AMPSA) |
|---|---|
| $\begin{array}{c} R \\ \| \\ H_2C{=}C \\ \| \\ C{=}O \\ \| \\ O \\ \| \\ R^1 \end{array}$ | $\begin{array}{c} R \\ \| \\ H_2C{=}C \\ \| \\ C{=}O \\ \| \\ NH \\ \| \\ CH_3{-}C{-}CH_3 \\ \| \\ CH_2 \\ \| \\ SO_3^- \ X^+ \end{array}$ | where R is H or $CH_3$; $R^1$ is $X^+$, H, $C_{1-4}$alkyl, $CH_2CH_2OH$, $(CH_2CH_2O-)_x-H$, where x = 1-50, or phenyl, and $X^+$ is a suitable cation forming a salt of the carboxylic or sulfonic acid.

7. A method according to claim 6 wherein the weight percent of AM is from 10 to 80, the weight percent of DMDAAC is from 15 to 60, and the weight percent of AMPSA is from 5 to 40.

8. A method according to claim 7 wherein the ampholyte terpolymer is a member selected from the group consisting of:

| WT. % | POLYMER COMPOSITION | |
|---|---|---|
| AM | DMCAAC | AMPSA |
| 50 | 22 | 28 |
| 50 | 30 | 10 + 10 AA |
| 50 | 15 | 35 |
| 50 | 40 | 10 |
| 60 | 30 | 10 |
| 49 | 37 | 14 |
| 50 | 40 | 10 |

-continued

| WT. % | POLYMER COMPOSITION | |
|---|---|---|
| AM | DMCAAC | AMPSA |
| 16 | 32 | 52 |

9. A method according to claim 6 wherein the ampholyte terpolymer has a molecular weight of from about 500 thousand to about 5 million.

10. A method according to claim 6 wherein the cosmetically acceptable medium is an anionic surfactant-containing shampoo.

11. A method of treating hair in conjunction with the shampooing thereof with an anionic sufactant-containing shampoo, so as to improve the conditioning thereof with respect to the properties of detangling, wet combability, wet feel, dry combability, dry feel, sheen, static flyaway control, and curl retention comprising applying to said hair a composition compatible with said anionic surfactant-containing shampoo such that a clear formulation thereof is provided without the loss of said conditioning properties, wherein said composition comprises a cosmetically acceptable medium containing from 0.1-10% by weight of a water-soluble an ampholyte terpolymer having a weight average molecular weight of from about 10 thousand to 10 million, comprising:

(a) from at least 1 to as much as 95 weight percent of the nonionic monomer acrylamide (AM) of the following formula:

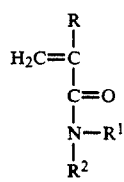

where R is H or $CH_3$; and $R^1$ and $R^2$ are independently H, $C_{1-4}$alkyl, $CH_2OCH_3$, $CH_2OCH_2CH(CH_3)_2$, $(CH_2CH_2O-)_x-H$, where $x=1-50$, or phenyl, or together are $C_{3-6}$cycloalkyl;

(b) from at least 5 to as much as 80 weight percent of the cationic monomer dimethyldiallylammonium chloride (DMDAAC) of the following formula:

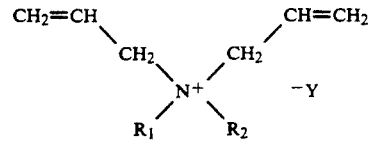

where $R_1$ and $R_2$ are independently H or $C_{1-2}$alkyl, and the moiety $-Y$ is a suitable anion; and (c) from at least 1 to as much as 75 weight percent of the anionic monomer 2-acrylamido-2-methylpropane sulfonic acid (AMPSA), with optionally up to 50% of said anionic monomer AMPSA being replaced with the anionic monomer acrylic acid (AA), both of the following formulas:

| Acrylic Acid (AA) | 2-Acrylamido-2-methylpropane Sulfonic Acid (AMPSA) |
|---|---|
| $\begin{array}{c} R \\ | \\ H_2C=C \\ | \\ C=O \\ | \\ O \\ | \\ R^1 \end{array}$ | $\begin{array}{c} R \\ | \\ H_2C=C \\ | \\ C=O \\ | \\ NH \\ | \\ CH_3-C-CH_3 \\ | \\ CH_2 \\ | \\ SO_3^- \ X^+ \end{array}$ | where R is H or $CH_3$; $R^1$ is $X^+$, H, $C_{1-4}$alkyl, $CH_2CH_2OH$, $(CH_2CH_2O-)_x-H$, where $x=1-50$, or phenyl, and $X^+$ is a suitable cation forming a salt of the carboxylic or sulfonic acid.

12. A method according to claim 6 wherein the weight percent of AM is from 10 to 80, the weight percent of DMDAAC is from 15 to 60, and the weight percent of AMPSA is from 5 to 40.

13. A method according to claim 12 wherein the ampholyte terpolymer is a member selected from the group consisting of:

| WT. % | POLYMER COMPOSITION | |
|---|---|---|
| AM | DMCAAC | AMPSA |
| 50 | 22 | 28 |
| 50 | 30 | 10 + 10 AA |
| 50 | 15 | 35 |
| 50 | 40 | 10 |
| 60 | 30 | 10 |
| 49 | 37 | 14 |
| 50 | 40 | 10 |
| 16 | 32 | 52 |

14. A method according to claim 11 wherein the ampholyte terpolymer has a molecular weight of from about 500 thousand to about 5 million.

15. A method according to claim 11 wherein the cosmetically acceptable medium is an anionic surfactant-containing shampoo.

* * * * *